(12) United States Patent
Chuter

(10) Patent No.: US 8,632,581 B2
(45) Date of Patent: Jan. 21, 2014

(54) CONFORMABLE END SEALING STENT

(75) Inventor: Timothy A. M. Chuter, San Francisco, CA (US)

(73) Assignee: Cook Medical Technologies LLC, Bloomington, IN (US)

( * ) Notice: Subject to any disclaimer, the term of this patent is extended or adjusted under 35 U.S.C. 154(b) by 1457 days.

(21) Appl. No.: 11/825,473

(22) Filed: Jul. 6, 2007

(65) Prior Publication Data

US 2008/0015673 A1 Jan. 17, 2008

Related U.S. Application Data

(60) Provisional application No. 60/819,978, filed on Jul. 10, 2006.

(51) Int. Cl.
*A61F 2/90* (2013.01)

(52) U.S. Cl.
USPC .......................... 623/1.13; 623/1.51; 623/1.53

(58) Field of Classification Search
USPC ....................... 623/1.13, 1.22, 1.32
See application file for complete search history.

(56) References Cited

U.S. PATENT DOCUMENTS

| | | | |
|---|---|---|---|
| 2002/0038142 A1* | 3/2002 | Khosravi et al. | 623/1.13 |
| 2002/0156522 A1* | 10/2002 | Ivancev et al. | 623/1.13 |
| 2003/0040771 A1* | 2/2003 | Hyodoh et al. | 606/200 |

* cited by examiner

*Primary Examiner* — David H Willse
*Assistant Examiner* — Tiffany Shipmon
(74) *Attorney, Agent, or Firm* — Brinks Gilson & Lione

(57) ABSTRACT

Conformable end sealing stent for treating aortic aneurysms with acute angulation having an end portion with a circumference and configured to exert a radial force against an inner wall of the aorta, said end portion comprised of one or more filaments formed into at least three intertwined curved loops, each loop having a first and second end and a curved section which curved section is shaped and sized to extend at least halfway around the circumference.

18 Claims, 4 Drawing Sheets

CONFORMABLE END SEALING STENT

This application claims priority to U.S. Provisional Application No. 60/819,978 filed Jul. 10, 2006, which is hereby incorporated herein by reference in its entirety.

BACKGROUND

1. Technical Field

This invention relates to a medical device for implantation within the human or animal body for the repair of aortic aneurysms.

2. Background Information

In general, as a thoracic aortic aneurysm dilates, its length also increases. Distally this creates a transverse segment above the diaphragm. Proximally, this pushes the distal arch in a cranial direction, often causing the aorta to buckle at the top of the aneurysm. This makes the arch more difficult to traverse with a delivery system. Nevertheless, some solutions have been presented. For example, trackable, kink-resistant sheaths have been developed that will follow a stiff guidewire around almost any bend in the aorta.

However, the more difficult problem is stent-graft implantation. To function effectively, a proximal end of the stent graft has to occupy a co-axial position with the distal aortic arch of the implantation site while the rest of the graft has to traverse the long axis of-the aneurysm, which lies in a very different direction. The bending moment imposed upon the proximal end of the stent-graft is required to overcome the stiffness of the rest of the implant and induce bending but not kinking. Naturally, kinking may restrict the flow of blood through the implant. In general, the longer the implantation site, the greater the influence of aortic axis on proximal stent axis. The stiffer the stent graft, the greater the resistance to that influence.

Flexibility of a stent graft can be limited by a number of factors. Flexibility is sometimes sacrificed to provide dimensional stability or column strength. Some stents lack flexibility when there is little or no differential shortening or lengthening. Attaching a graft to the stent can also limit the flexibility.

Flexible stent-grafts typically have short, widely spaced stents. Most designs do not permit stent overlapping because the ends are all attached to fabric to prevent movement and graft erosion.

The length of the implantation site may also be limited by the proximity of the aneurysm to the arch vessels because covered stents cannot encroach on arterial orifices without causing occlusion, which can lead to a stroke. Uncovered stents have been known to cause erosion of the soft, curved, mobile aortic arch.

BRIEF SUMMARY

The present invention provides a stent for sealing an end of a prosthesis used to treat an aneurysm with acute angulation. The stent has an end portion with a circumference and is configured to exert a radial force against an inner wall of the aorta. The end portion is comprised of one or more filaments formed into at least three intertwined curved loops. Each of these loops have a first and second point and a curved section that is shaped and sized to extend at least halfway around the circumference. In another embodiment, the stent may be an end component to an endoluminal prosthesis for treating an aortic aneurysm with acute angulation. The prosthesis comprises a descending component for implantation substantially along the descending aorta connected by a flexion segment to an end component for implantation within at least a portion of the arch of the aorta. The descending component comprises an elongated tube such as a stent graft.

The stent of the present invention may be made of more than one filament. The filament may be comprised of a single strand in one embodiment or of multiple strands in another embodiment. Multiple strand embodiments may be comprised of twisted or braided filaments. The stent preferably exerts some radial force against the endoluminal wall or flexion segment in some embodiments.

DETAILED DESCRIPTION OF THE DRAWINGS AND THE PREFERRED EMBODIMENTS

Figure 1:
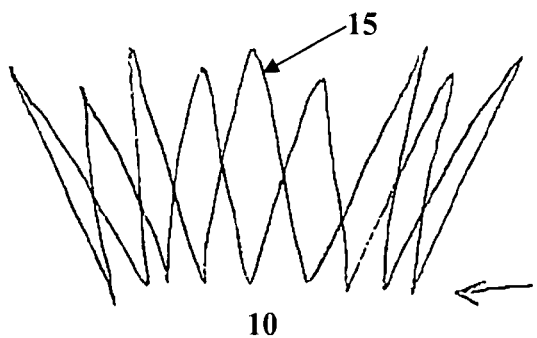
FIG. 1 is a perspective view of the crowned end of a Z-stent used in the prior art.

The structural components such as the filament may be made from numerous base materials such as biocompatible metals or other metallic materials. For example, the structural components may be made of polymers including bioabsorbable or biostable polymers; stainless steels (e.g., 316, 316L or 304); nickel-titanium alloys including shape memory or superelastic types (e.g., nitinol or elastinite); noble metals including platinum, gold or palladium; refractory metals including tantalum, tungsten, molybdenum or rhenium; stainless steels alloyed with noble and/or refractory metals; silver; rhodium; inconel; iridium; niobium; titanium; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; nonmetallic biocompatible materials including polyamides, polyolefins (e.g., polypropylene or polyethylene), nonabsorbable polyesters (e.g., polyethylene terephthalate) or bioabsorbable aliphatic polyesters (e.g., homopolymers or copolymers of lactic acid, glycolic acid, lactide, glycolide, para-dioxanone, trimethylene carbonate or epsilon.-caprolactone); polymeric materials (e.g., poly-L-lactic acid, polycarbonate, polyethylene terephthalate or engineering plastics such as thermotropic liquid crystal polymers (LCPs)); biocompatible polymeric materials (e.g., cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene or polytetrafluoroethylene); degradable or biodegradable polymers, plastics, natural (e.g., animal, plant or microbial)

or recombinant material (e.g., polylactic acid, polyglycolic acid, polyanhydride, polycaprolactone, polyhydroxybutyrate valerate, polydepsipeptides, nylon copolymides, conventional poly(amino acid) synthetic polymers, pseudo-poly (amino acids) or aliphatic polyesters (e.g., polyglycolic acid (PGA), polylactic acid (PLA), polyalkylene succinates, polyhydroxybutyrate (PHB), polybutylene diglycolate, poly epsilon-caprolactone (PCL), polydihydropyrans, polyphosphazenes, polyorthoesters, polycyanoacrylates, polyanhydrides, polyketals, polyacetals, poly(alpha.-hydroxy-esters), poly(carbonates), poly(imino-carbonates), poly(beta.-hydroxy-esters) or polypeptides); polyethylene terephthalate (e.g., Dacron® or Mylar®); expanded fluoropolymers (e.g., polytetrafluoroethylene (PTFE); fluorinated ethylene propylene (FEP); copolymers of tetrafluoroethylene (TFE) and per fluoro(propyl vinyl ether) (PFA)); homopolymers of polychlorotrifluoroethylene (PCTFE) and copolymers with TFE; ethylene-chlorotrifluoroethylene (ECTFE); copolymers of ethylene-tetrafluoroethylene (ETFE); polyvinylidene fluoride (PVDF); polyvinyfluoride (PVF); polyaramids (e.g., Kevlar®); polyfluorocarbons including polytetrafluoroethylene with and without copolymerized hexafluoropropylene (e.g., Teflon® or Goretex®); expanded fluorocarbon polymers; polyglycolides; polylactides; polyglycerol sebacate; polyethylene oxide; polybutylene terephthalate; polydioxanones; proteoglymays; glycosaminoglymays; poly(alkylene oxalates); polyalkanotes; polyamides; polyaspartimic acid; polyglutarunic acid polymer; poly-p-diaxanone (e.g., PDS); polyphosphazene; polyurethane including porous or nonporous polyurethanes; poly (glycolide-trimethylene carbonate); terpolymer (copolymers of glycolide, lactide or dimethyltrimethylene carbonate); polyhydroxyalkanoates (PHA); polyhydroxybutyrate (PHB) or poly(hydroxybutyrate-co-valerate) (PHB-co-HV); poly (epsilon-caprolactone) (e.g., lactide or glycolide); poly(epsilon-caprolactone-dimethyltrimethylene carbonate); polyglycolic acid (PGA); poly-L and poly-D(lactic acid) (e.g., calcium phosphate glass); lactic acid/ethylene glycol copolymers; polyarylates (L-tyrosine-derived) or free acid polyarylates; polycarbonates (tyrosine or L-tyrosine-derived); poly (ester-amides); poly(propylene fumarate-co-ethylene glycol) copolymer (e.g., fumarate anhydrides); polyanhydride esters; polyanhydrides; polyorthoesters; prolastin or silk-elastin polymers (SELP); calcium phosphate (bioglass); compositions of PLA, PCL, PGA ester; polyphosphazenes; polyamino acids; polysaccharides; polyhydroxyalkanoate polymers; various plastic materials; Teflon®; nylon; block polymers or copolymers; Leica RM2165; Leica RM2155; organic fabrics; biologic agents (e.g., protein, extracellular matrix component, collagen, fibrin); small intestinal submucosa (SIS) (e.g., vacuum formed SIS); collagen or collagen matrices with growth modulators; aliginate; cellulose and ester; dextran; elastin; fibrin; gelatin; hyaluronic acid; hydroxyapatite; polypeptides; proteins; ceramics (e.g., silicon nitride, silicon carbide, zirconia or alumina); bioactive silica-based materials; carbon or carbon fiber; cotton; silk; spider silk; chitin; chitosan (NOCC or NOOC-G); urethanes; glass; silica; sapphire; composites; any mixture, blend, alloy, copolymer or combination of any of these; or various other materials not limited by these examples.

The term "stent" means any device that provides rigidity, expansion force and/or support to the lumen of an anatomical vessel. In one configuration, the stent may be a plurality of discontinuous devices, for example a series of rings. In another configuration, the stent may be one device, for example a mesh device. Stents may have a wide variety of configurations and may be balloon-expandable, self-expanding, or a combination of the two. Typically, stents have a circular cross-section when fully expanded, so as to conform to the generally circular cross-section of a body lumen. In one example, a stent may comprise struts and acute bends or apices that are arranged in a zig-zag configuration in which the struts are set at angles to each other and are connected by the acute bends.

A variety of biocompatible materials may be employed to construct the stent, or portions of the stent, including metals and/or alloys, medically-acceptable polymers, and/or bioabsorbable polymers or materials. The metals and/or alloys may, among other things, include stainless steel, tantalum, nitinol, gold, silver, tungsten, platinum, inconel, cobalt-chromium alloys, and iridium, all of which are commercially available metals or alloys used in the fabrication of medical devices. In one configuration, the stent is constructed from nitinol, stainless steel, and/or cobalt-chromium alloys.

"Biocompatible" describes something that may be substantially non-toxic in the in vivo environment of its intended use, and is not substantially rejected by the patient's physiological system (i.e., is non-antigenic). This may be gauged by the ability of a material to pass the biocompatibility tests set forth in International Standards Organization (ISO) Standard No. 10993 and/or the U.S. Pharmacopeia (USP) 23, and/or the U.S. Food and Drug Administration (FDA) blue book memorandum No. G95-1, entitled "Use of International Standard ISO-10993, Biological Evaluation of Medical Devices Part 1: Evaluation and Testing." Typically, these tests measure a material's toxicity, infectivity, pyrogenicity, irritation potential, reactivity, hemolytic activity, carcinogenicity, and/or immunogenicity. A biocompatible structure or material, when introduced into a majority of patients, will not cause a significantly adverse reaction or response. Furthermore, biocompatibility may be affected by other contaminants such as prions, surfactants, oligonucleotides, and other agents or contaminants.

The present invention provides a stent for sealing an end of a prosthesis used to treat aortic aneurysms with acute angulation, such as a thoracic aortic aneurysm, for example. The end sealing stent has an end portion with a circumference and is configured to exert a radial force against an inner wall of the aorta. Some embodiments have two end portions. The end portion is comprised of one or more filaments formed into at least three intertwined curved loops. Each loop has a first and second point and a curved section that is shaped and sized to extend at least halfway around the circumference. The loops minimize the potential for injury to vessel walls as well as damage to grafts by having no sharp apices.

The filament or filaments may also comprise the stent body section. The stent body can be lightly corrugated or braided to provide stability to the stent body but also allow blood to flow through the body. The filaments may be comprised of metal or polymer. The filaments may also be multi-stranded or single stranded. In some multi-stranded embodiments, the strands may be twisted or braided.

Figure 2:
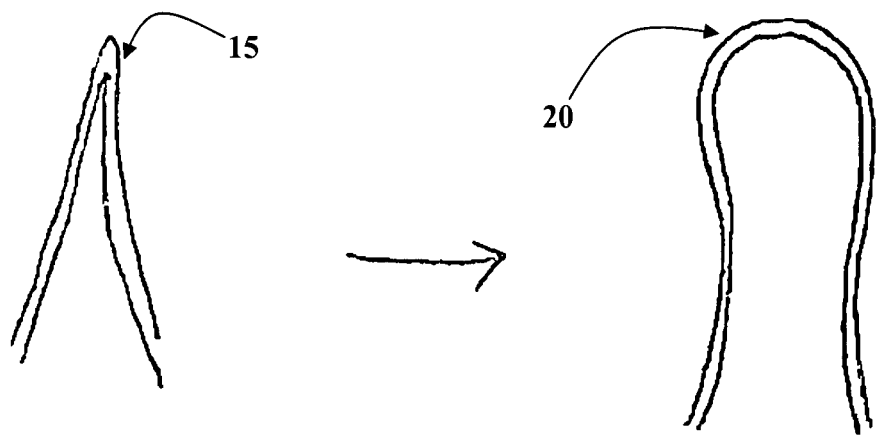
FIG. 2 is an apex found in the prior art shown on the left and a curved loop of the present invention on the right.

Z-stents can flower out into a non-cylindrical pattern 10, such as the frusto-conical shape shown in FIG. 1. In FIG. 2, the apex 15, characteristic of the Z-stent, is replaced with a curve 20 that is less acute. However, this can make packing a stent difficult, especially if all the curves are at the same level. The curves may also project away from the wall of the aorta, disturbing flow and promoting thrombus deposition in areas of turbulence. Therefore, the curve is widened further such that it loops around the opposite wall of the aorta to provide a blunt and wide loop on the end portion.

Figure 3A:
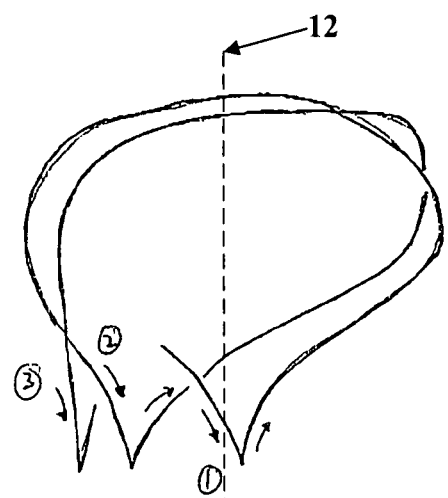
FIG. 3A is a perspective view of intertwining curved loops partially forming the end portion of a stent.
Figure 3B:
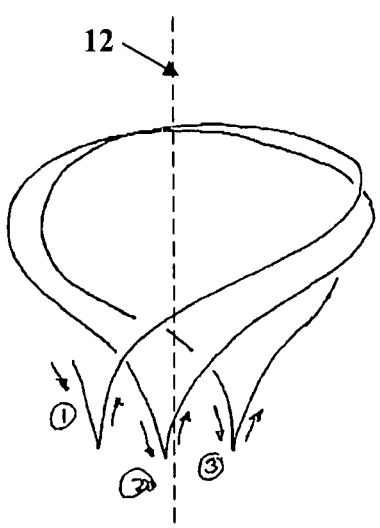
FIG. 3B is a perspective view of intertwining curved loops partially forming the end portion of a stent by an alternate method.

Examples of how the curved loops form the end portion are shown in FIGS. 3A and 3B. In FIG. 3A, a portion of the filament forms two intertwined curved loops starting at a first point 1 and curving around the axis 12 of the stent body to a second point 2 that is to the left, or just before, the first point 1. As a result, the curved loop section extends 50%, or at least halfway, around the circumference of the end portion. After leaving the second point 2 the loop curves around the circumference once more to point 3, which is to the left, or just before the second point 2. As described, the curved loop extends at least 50%, or halfway, around the circumference of the of the end portion.

In an embodiment where the stent is comprised of one filament, the filament exits and enters the stent body section at a point to the left of, or just before, a previous point. For instance, a section of filament enters into the stent body section (not shown) at the first point 1 and proceeds in the direction of the arrow down the body of the stent. The filament returns from the stent body section (not shown) to the first point 1 and curves around the axis 12 of the stent to the second point 2, which is to the left of, or just before, the first point 1. The filament then proceeds down the body of the stent in a helical manner. A filament then returns to the second point 2 to curve around the axis 12 and enter the ring of the stent before coming to point 3, which is to the left of, or just before, the second point 2. The filament continues in this manner until it comes to the right, or just beyond, the first point 1.

Figure 4:
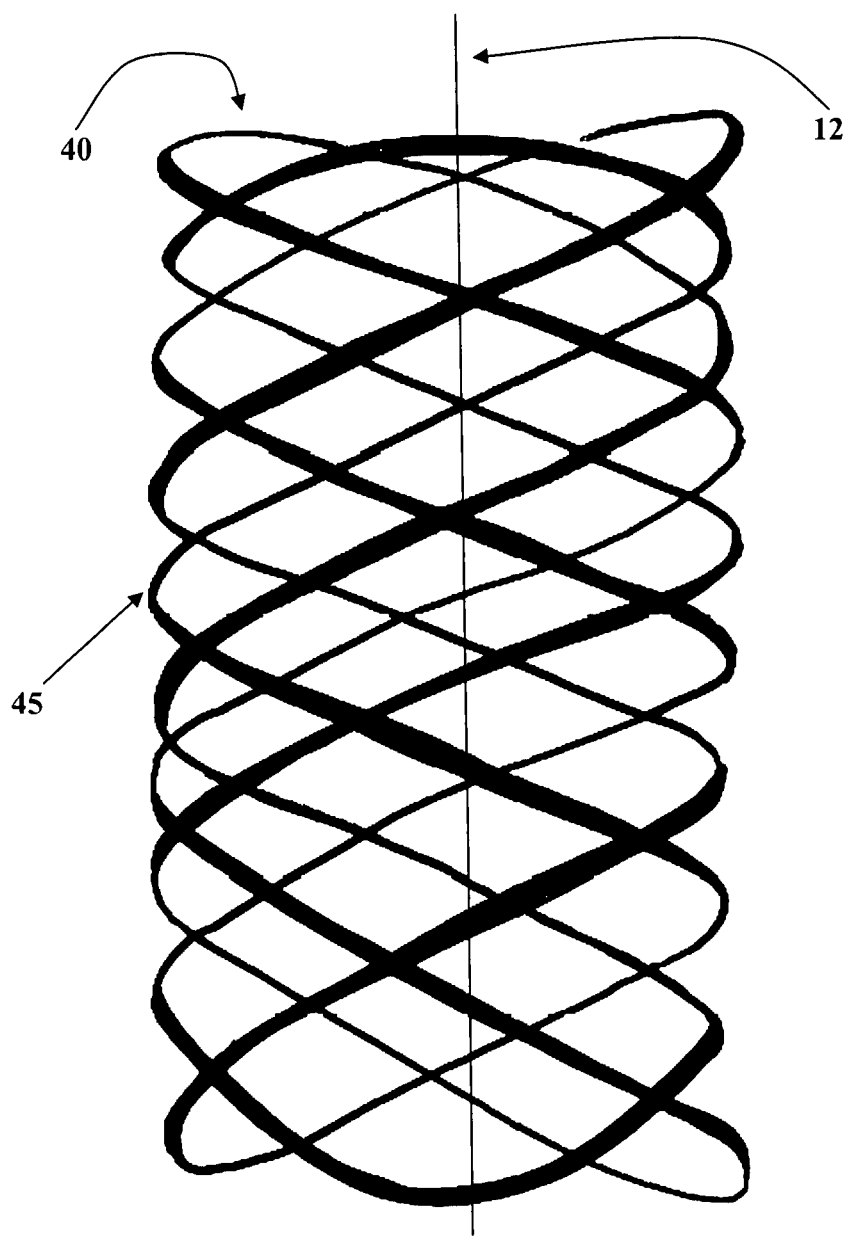
FIG. 4 is a perspective view of one end of a braided stent with curved loops forming end portions of the stent.

In FIG. 3B, a portion of the filament forming two intertwined curved loops starting at a first point 1 and curving around the axis 12 of the stent body to a second point 2 that is to the right, or just after, the first point 1. The filament then curves from the second point 2 around the axis 12 to point 3. In embodiments comprising one filament, the section of the filament that forms the curved loop exits and enters the stent body section (not shown) at a point to the right, or just after, the previous point in a similar manner as previously described. The filament continues in this manner until it comes to the left, or just before, the first end 1. In this embodiment, the loop extends around the circumference of the end portion over 100%. An embodiment with end loops formed at both ends of a braided stent can be seen in FIG. 4.

The loops 40 cross one another in opposite directions while retaining the apical connections. Once expanded, the loops 40 are more robust than Gianturco Z-stent-type ends. The loops of the present invention also contribute to the shortening of the stent. Stent strength, its resistance to compression, and the energy that drives the stent expansion, come not from the braided body section 45, but from the loop 40. The loop 40 also undergoes a far greater local deformation, or strain, during stent collapse or expansion.

The end sealing stent may be from about 1 cm to about 6 cm in length or any combination or subcombination therein. In some embodiments, the stent may be from about 2 cm to about 3 cm in length. Generally speaking, the stent may be made to accommodate any predetermined size.

Figure 5:
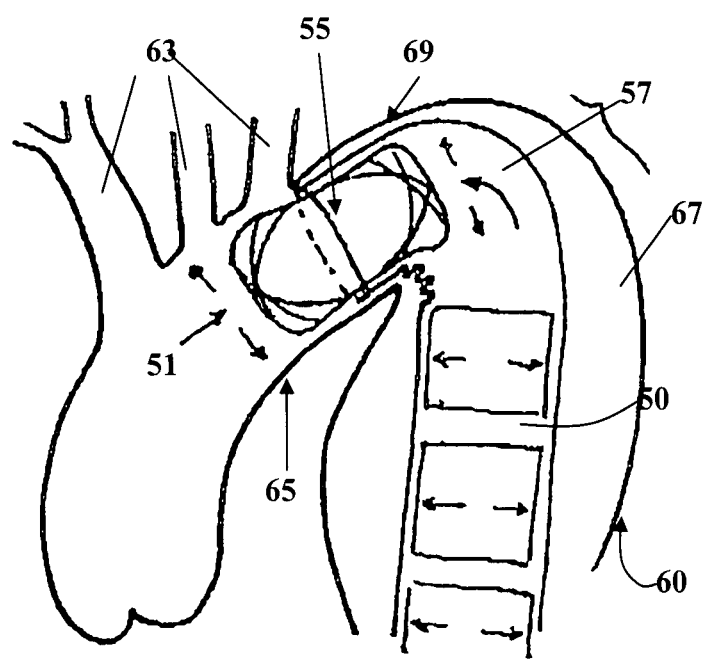
FIG. 5 is an endoluminal prosthesis with an end sealing stent within a thoracic aortic aneurysm.

In FIG. 5, another embodiment of the present invention, an endoluminal prosthesis for treating aneurysms with acute angulation, is shown in a thoracic aortic aneurysm. The prosthesis comprises two parts: a descending component 50 for implantation substantially along the descending 60 portion of the aorta and an end sealing stent 55 of the present invention for implantation at least partially in the arch of the aorta 67. In some embodiments, the end sealing stent 55 may be implanted at least partially into the ascending 65 portion of the aorta. The two parts are connected by a flexion segment 57 that extends along the arch 67 of the aorta to meet with the end sealing stent 55. In some embodiments, the flexion segment is not supported by a stent, but is comprised of graft material. The descending component 50 comprises an elongated tube, such as an elongated tube made of biocompatible graft material coupled to an expandable stent. The graft material is generally resilient or elastic in the longitudinal direction and can be made of polyester, polytetrafluoroethylene (PTFE), or similar commonly used graft material.

The multiple winds provided by the loops of the end sealing stent 55 provide a seal with the flexion segment 57 and the aortic wall 69. The loops apply radially directed force over a short, transaxial segment. Even in the presence of irregularity, angulation, short overlap zone, or implantation site, each loop formed contributes independently to the seal. The cumulative effect is close apposition between the graft and aorta.

Because of the relative small size of the end sealing stent 55, it does not occlude the arch vessels 63 or attract significant amounts of thrombus. Also, in some embodiments where the end sealing stent 55 is not covered or embedded in graft material, blood flow is not significantly occluded. In other embodiments, the end sealing stent 55 is covered or embedded in graft material. The stent 55 may be formed with eyelets in the braided body section 45 such that graft may be stitched thereto. The end sealing stent 55 may also exert radial pressure on the flexion segment 57.

The prosthesis may be deployed via methods known in the art, including the method described in PCT Patent Publication Number No. WO98/53761. In this method, the prosthesis is inserted by an introducer via a surgical cut-down into a femoral artery. The prosthesis is then advanced into the desired position over a stiff wire guide using endoluminal interventional techniques known in the art.

Throughout this specification, various indications have been given as to preferred and alternative embodiments of the invention. However, it should be understood that the invention is not limited to any one of these. It is therefore intended that the foregoing detailed description be regarded as illustrative rather than limiting, and that it be understood that it is the appended claims, including all equivalents, that are intended to define the spirit and scope of this invention.

The invention claimed is:

1. A stent for sealing an end of a prosthesis used to repair an aortic aneurysm with acute angulation, the stent having a body section and an end portion with a circumference and configured for exerting an outward radial force, said end portion comprised of one or more filaments formed into at least three intertwined curved end loops, where each curved end loop has a curved section that extends at least halfway around the circumference of the end portion.

2. The stent of claim 1 wherein the curved section extends over 100% around the circumference.

3. The stent of claim 1 wherein the filament is comprised of metal or polymer.

4. The stent of claim 1 wherein the filament comprises a single strand or multiple strands.

5. The stent of claim 3 wherein the multiple strands are twisted or braided.

6. The stent of claim 1 wherein graft material is attached to the stent.

7. The stent of claim 6 being from about 2 cm to about 3 cm in length.

8. The stent of claim 1 being from about 1 cm to about 6 cm in length.

9. An endoluminal prosthesis for treating a thoracic aortic aneurysm comprising a descending component for implantation substantially along the descending aorta connected by a flexion segment to an end component for implantation within at least a portion of the arch of the aorta, the descending component comprising an elongated tube made of biocompatible graft material coupled to an expandable stent; and the end component comprising a stent having a body section and an end portion with a circumference and configured for exerting an outward radial force, said end portion comprised of one or more filaments formed into at least three intertwined curved end loops, where each curved end loop has a curved section that extends at least halfway around the circumference of the end portion.

10. The endoluminal prosthesis of claim 9 wherein the end component exerts radial pressure on the flexion segment.

11. The endoluminal prosthesis of claim 9 wherein the curved end loops exert radial pressure on an endoluminal wall.

12. The endoluminal prosthesis of claim 9 wherein the curved section extends over 100% around the circumference.

13. The endoluminal prosthesis of claim 9 wherein the filament is comprised of metal or polymer.

14. The endoluminal prosthesis of claim 9 wherein the filament comprises a single strand or multiple strands.

15. The endoluminal prosthesis of claim 14 wherein the multiple strands are twisted or braided.

16. The endoluminal prosthesis of claim 9 wherein graft material is attached to the end component.

17. The endoluminal prosthesis of claim 9 being from about 1 cm to about 6 cm in length.

18. The endoluminal prosthesis of claim 17 being from about 2 cm to about 3 cm in length.

* * * * *